US00PP34266P2

(12) United States Plant Patent
Hansen

(10) Patent No.: US PP34,266 P2
(45) Date of Patent: May 24, 2022

(54) ***BUDDLEIA* PLANT NAMED 'GOLD DROP'**

(50) Latin Name: ***Buddleia* hybrid**
Varietal Denomination: Gold Drop

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/803,083

(22) Filed: Feb. 1, 2022

(51) Int. Cl.
*A01H 6/00* (2018.01)
*A01H 5/02* (2018.01)

(52) U.S. Cl.
USPC ..... Plt./242

(58) Field of Classification Search
USPC ..... Plt./242
See application file for complete search history.

*Primary Examiner* — Annette H Para

(57) ABSTRACT

The new and distinct cultivar of ornamental, hardy Butterfly Bush plant named *Buddleia* 'Gold Drop' is a compact, open, round-mounded, multi-stemmed, compact, arching, winter-hardy butterfly bush with many-flowered compact thyrse starting early and over a long season beginning mid-summer, from soil line to top of plant, with sweetly-fragrant deep-purple to deep reddish-purple flowers that are attractively offset by light yellow to vivid yellow foliage.

1 Drawing Sheet

Botanical classification: *Buddleia* hybrid.
Variety denomination: 'Gold Drop'.

STATEMENT REGARDING PRIOR DISCLOSURES UNDER 37 CFR 1.77(B)(6)

The first public disclosure of the claimed plant, in the form of a sale, was made by Walters Gardens, Inc. on Oct. 18, 2021 to Forest Lakes Nursery and Burpee Co. Prior to that, on Feb. 1, 2021 the claimed plant was displayed with a non-enabling photograph and brief description in a website operated by Walters Gardens, Inc., and on May 21, 2021 as a non-enabling photograph and brief description in the "Walters Gardens 2021-2022 Catalog" by Walters Gardens, Inc., who obtained the plant and all information relating thereto, from the inventor. No plants of *Buddleia* 'Gold Drop' were in condition to sell prior to the first sale date, nor have been sold, in this country or anywhere in the world, nor has any disclosure of the new plant been made more than one year prior the filing date of this application, and such sale or disclosure within one year was either derived directly or indirectly from the inventor.

BACKGROUND OF THE PLANT

The present invention relates to the new and distinct butterfly bush plant in the Scrophulariaceae family, *Buddleia* 'Gold Drop' hereinafter also referred to as the new plant or by the cultivar name, 'Gold Drop'. Seed from which the new plant was selected was collected by the inventor on Oct. 18, 2014 at a wholesale perennial nursery in Zeeland, Mich., USA. 'Gold Drop' is the result of an ongoing breeding program conducted by the inventor. The goals for this program have been to produce improved, garden-worthy plants for the ornamental plant market with quality flowers, foliage and habit. The new plant, originally assigned breeder code 14-1-4, is a single plant selected from among multiple seedlings of an insect pollination of the proprietary unreleased hybrid named 12-83-1 (not patented) as the female or seed patent. The male parent would be a one of a number of unnamed siblings of 12-83-1 (not patented).

*Buddleia* 'Gold Drop' was first asexually propagated from a single select plant in 2019 by stem cuttings at the same nursery in Zeeland, Mich. The resultant asexually propagated plants have been found to be stable and true to type in successive generations of asexual reproduction.

SUMMARY OF THE INVENTION

Plants of the new *Buddleia* have not been observed under all possible environmental conditions. The phenotype may vary somewhat with variations in environment and cultural practices such as temperature, light intensity, available moisture and fertility without, however, any variance in genotype.

The following traits have been repeatedly observed and are determined to be the unique characteristics of 'Gold Drop'.

The nearest comparison plant are: *Buddleia* 'Crown Jewels' U.S. Plant Pat. No. 27,878, 'Evil Ways' (not patented), 'Little Nugget' U.S. Plant Pat. No. 28,152, 'Crown Jewels' is taller and broader in habit. 'Evil Ways' has a taller habit and larger foliage. 'Little Nugget' has a larger, less compact and taller habit, the foliage is more chartreuse and not as bright yellow, and the contrast between the flower color and foliage color has a less reddish-purple hue. 'Santana' U.S. Plant Pat. No. 12,383 is variegated and has a yellow to chartreuse leaf margin along with a medium green leaf center.

The female parent and the male parent have foliage that is not as brightly yellow-colored, the habit is not as short and dense and the contrast between flower color and foliage color was a less reddish-purple hue.

*Buddleia* 'Gold Drop' is a unique winter-hardy butterfly bush different from all other *Buddleia* cultivars known to the inventor based on the following combined traits:

1. Winter-hardy shrub, with multiple-stemmed, well-branched, compact, dense, arching, round-mounded habit;
2. Many-flowered compact thyrse starting early and over a prolonged season beginning mid-summer and continuing until frost from soil line to top of plant;
3. Flowers of deep purple to reddish purple;
4. Lanceolate foliage of light to vivid yellow.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
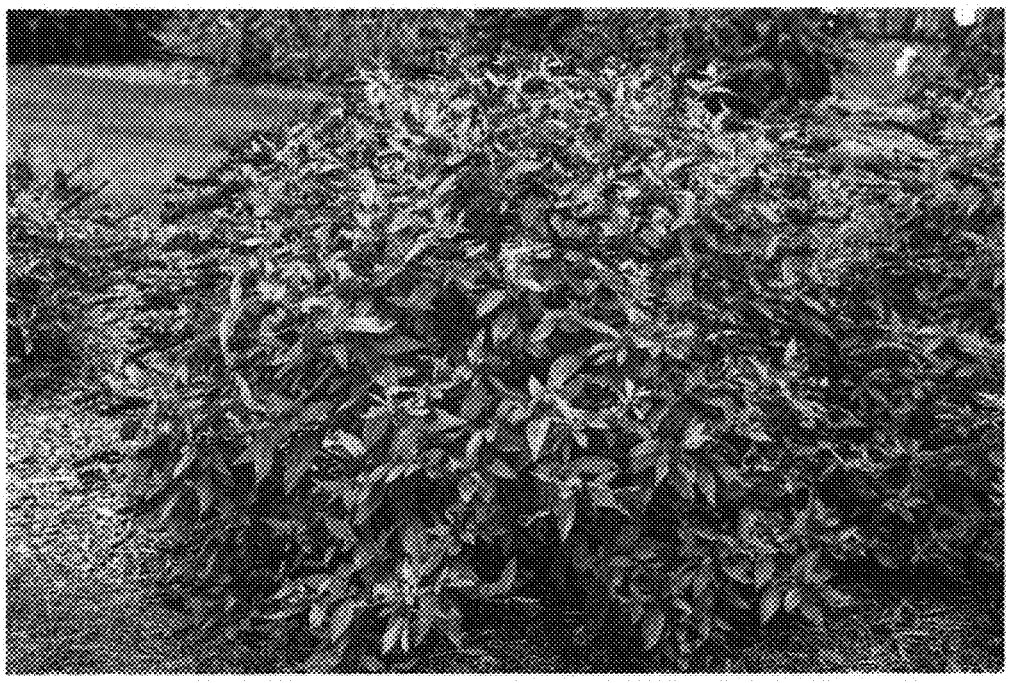
FIG. 1 shows the habit of a three-year-old plant in mid-season flowering.
Figure 2:
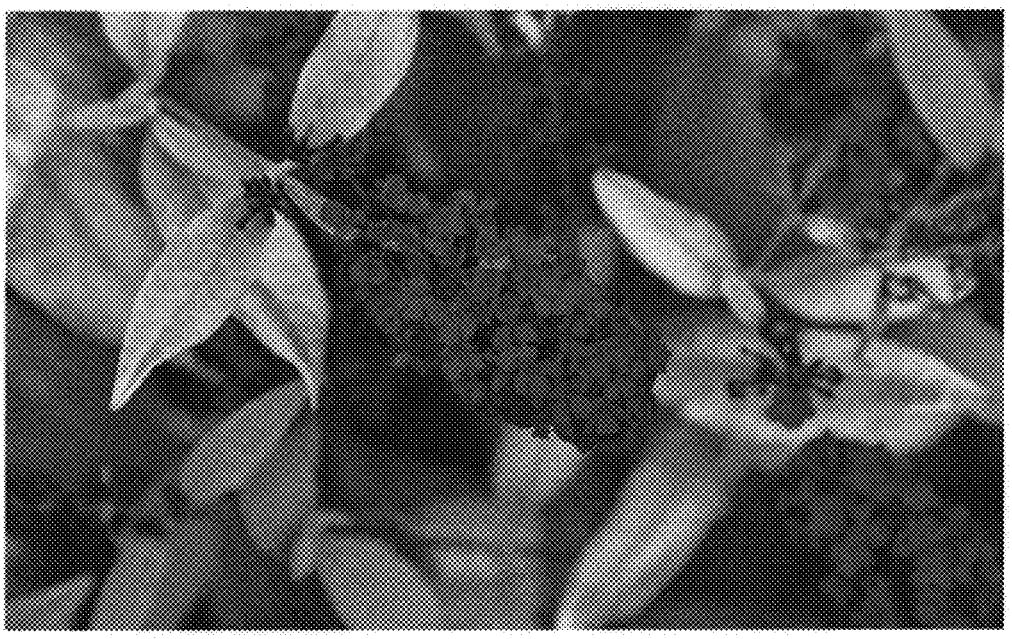
FIG. 2 shows a close-up of the flowers with buds near apex.

The following descriptions and color references are based on the 2001 edition of The Royal Horticultural Society Colour Chart except where common dictionary terms are used. The new plant, *Buddleia* 'Gold Drop', has not been observed under all possible environments. The phenotype may vary slightly with different environmental conditions, such as temperature, light, fertility, moisture and maturity levels, but without any change in the genotype. The following observations and size descriptions are of six-year-old plants in the loamy-sand, open-sun, field trials of a nursery in Zeeland, Mich. with supplemental fertilizer and water as needed. The plants are natural habit and were not treated with plant growth regulators, nor were they pinched at any time in the growth year except to cut back woody stems to about 15 cm tall in fall or early spring to promote new growth and flowering.

Parentage: Unreleased proprietary hybrid 12-83-1 (not patented) as the female or pod parent times an unnamed sibling of 12-83-1 as the male or pollen parent;

Propagation:

*Method*.—Softwood cuttings.

*Time to initiate roots*.—About two weeks.

*Rooting habit*.—Normal, dense and thick at base to about 1.5 cm diameter; fibrous, branching.

*Root color*.—Creamy white between RHS 159A and lighter than RHS 159 D depending on soil type.

*Crop time*.—Under normal spring growing conditions 6 to 7 weeks to fill and flower in a four-liter container a 65 mm liner; 8-10 weeks to finish and flower in a four-liter container from a 25 mm liner; Plant vigor is very good.

Plant description:

*Plant shape and habit*.—Winter-hardy, herbaceous, semi-woody, well-branched shrub with about 30 thick upright and branched main stems producing a dense, compact, arching, rounded mound.

*Plant size*.—About 115 cm tall and about 135 cm wide.

*Stem*.—Rounded and woody in lower portion, terete in cross section with exfoliating bark; younger upper portion puberulent and quadrangular in cross section with ridges in corners; strong and flexible; average about 90 cm tall from soil line to just below terminal flowers, and about 1 cm diameter at the base; before distal flowers about 10 to 12 branches per main stem extending at about 30° to 40° angle down from main stem.

*Stem color*.—Distal portion just below flowers between RHS N187A and RHS 187A on side exposed to high light levels and between RHS 146D and RHS 145A on side protected from high light, and in about the basal 20 to 30 cm between RHS 199B and RHS 197B with striations nearest RHS 156C.

*Internode*.—About 14 nodes per stem below flowers, average internode length about 6 cm on unpinched plant; upper internodes slightly more elongated than lower internodes. Node color: same as surrounding stem;

Foliage description: Opposite, decussate; serrulate; glabrescent adaxial, argenteous and farinose abaxial; lanceolate to elliptic; base attenuate; apex acute;

*Foliage fragrance*.—No foliar fragrance detected.

*Leaf blade size*.—To about 9.8 cm long and about 3.7 cm wide, average about 7.2 cm long and about 2.3 cm wide; becoming smaller in distal portion of stem.

*Foliage color*.—Variable; young expanding leaf adaxial side between RHS 14B and RHS 18B, young expanding abaxial between RHS 194D and RHS 193A; mature leaves adaxial side regions nearest RHS 137B and between RHS 11C and RHS 11D, mature abaxial nearest RHS 148D; late season leaves before frost adaxial nearest RHS 137A and abaxial between RHS 191A and RHS 194B.

*Veins*.—Reticulate; abaxial raised, adaxial slightly impressed.

*Vein color*.—Young expanding adaxial veins variable, nearest RHS 146C and nearest RHS 18B, abaxial young expanding veins nearest RHS 160D; mature adaxial veins nearest RHS 146D, abaxial veins nearest RHS 160C; late season adaxial nearest RHS 137B, abaxial veins midrib nearest RHS 146D and secondary veins nearest RHS 146B.

Petioles: Adaxial glabrous, abaxial farinose; concavo-convex; average size about 8 mm long and about 2 mm wide at the point of attachment to stem, average 3.5 mm long and 1.5 mm wide;

Petiole color: Nearest RHS 161D adaxial and between RHS 162D and RHS 195C abaxial;

Inflorescence description: Glomerate thyrse consisting of about 400 self-cleaning salverform flowers; to about 17.5 cm long and about 4.0 cm across; early, beginning in mid-July and continuing until late October in Michigan; attitude outwardly to slightly upward;

*Buds*.—Elongated clavate; apex rounded; one day prior to opening about 9 mm total length and about 2.5 mm diameter in club, throat about 1 mm diameter in throat and about 7.0 mm long.

*Bud color*.—Between RHS 77A and RHS N181A in club portion and tube portion nearest RHS N78A.

*Sepals*.—Four, proximal two-thirds connate, adpressed to corolla tube; acute apex; glabrous adaxial and farinose abaxial; margin entire, edentate; fused in about the basal 2.5 mm and split in about the terminal 0.5 mm; forming a corolla about 3 mm long and about 1 mm across; individually less than about 0.7 mm wide at point of fusion.

*Sepal color*.—Adaxial nearest RHS 144A in center and nearest RHS 183B along margins, abaxial nearest RHS 191C lightly tinted with nearest RHS N79C.

*Flowers fragrance*.—Pleasantly and distinctly sweet.

*Flower attitude*.—Upward and outward, not drooping.

*Lastingness of inflorescence*.—About 8 to 10 days.

*Lastingness of individual flower*.—About 3 to 5 days.

*Petals*.—Four; glabrous except distal 3 mm of adaxial corolla tube; fused into salverform with straight cylindrical tube about 8 mm long and 1 mm diameter, and a flattened face about 7.0 mm across; petal blade rounded with crenate margin; blade to about 3 mm across and about 3 mm long from fused face.

*Petal color*.—Adaxial tube center and distal throat nearest RHS 162B, tube base nearest RHS N187C, face between RHS N81A and RHS 77A; abaxial tube nearest RHS N77B with slight tinting of nearest RHS 71A, abaxial petal blades nearest RHS 77A.

*Gynoecium*.—Pistil: one; about 4 mm long. Style: short, round, glabrous; about 1.5 mm long and between about 0.2 mm and 0.3 mm diameter; color nearest RHS 145C moderately blushed with nearest RHS 187B; Stigma: bifid, lustrous; about 0.4 mm in diameter and less than 0.5 mm long; color nearest RHS 146B; Ovary: superior; ellipsoidal; about 0.7 mm across at base and about 2.0 mm tall; rounded apex, truncate base; color nearest RHS 147D.

*Androecium*.—Four. Filaments: typically not produced; Anthers: four; oblong; introrse; adnate to about midpoint of corolla tube; about 1 mm long and about 0.5 mm wide; color nearest RHS 158A; Pollen: numerous, globose, less than 0.1 mm across; color nearest RHS 158B.

Pedicel: short, puberulent; about 0.5 mm to 1.0 mm long and about 0.5 mm diameter; color lighter than RHS 194C;

Peduncle: Quadrangular, pubescent, stiff and strong; flowering portion to about 12 cm long and 20 cm wide;

Peduncle color: Between N187A and RHS 187A on portion facing sun, portion away from sun between RHS 146D and RHS 145A;

Fruit: Sparse fruit set; oblong with acute apex; glabrous, bi-valved, septicidal capsule; about 7 mm long and about 2 mm diameter and 2 mm thick;

Fruit color: As maturing nearest RHS 187A; when mature and dehiscing nearest RHS N199B;

*Seed*.—Elongated ellipse with sharply acute ends; less than about 2 mm long and about 0.1 mm diameter in center.

Seed color: Nearest RHS 200A;

Disease resistance: Resistance has been noted to deer browsing. Other resistance beyond that of known butterfly bush cultivars has not been observed.

Plant growth: The plant grows best with plenty of moisture and adequate drainage but tolerant of some drought when mature.

Hardiness: At least from USDA zone 6 through 10.

It is claimed:

1. A new cultivar of winter-hardy butterfly bush *Buddleia* plant named 'Gold Drop' as herein illustrated and described.

* * * * *